United States Patent
Pietron et al.

(10) Patent No.: US 11,027,258 B2
(45) Date of Patent: Jun. 8, 2021

(54) COPPER NANOPARTICLE-TITANIA COMPOSITE NANOARCHITECTURES

(71) Applicant: The Government of the United States of America, as represented by the Secretary of the Navy, Arlington, VA (US)

(72) Inventors: Jeremy J. Pietron, Washington, DC (US); Paul A. Desario, Alexandria, VA (US); Debra R. Rolison, Arlington, VA (US); Todd H. Brintlinger, Washington, DC (US); Rhonda Michele Stroud, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 282 days.

(21) Appl. No.: 15/472,782

(22) Filed: Mar. 29, 2017

(65) Prior Publication Data

US 2017/0282162 A1    Oct. 5, 2017

Related U.S. Application Data

(60) Provisional application No. 62/314,486, filed on Mar. 29, 2016.

(51) Int. Cl.
| | |
|---|---|
| *B01J 23/72* | (2006.01) |
| *B01J 35/00* | (2006.01) |
| *B01J 37/02* | (2006.01) |
| *C07D 301/03* | (2006.01) |
| *B01J 37/34* | (2006.01) |
| *C01B 3/10* | (2006.01) |

(Continued)

(52) U.S. Cl.
CPC ............ *B01J 23/72* (2013.01); *B01J 21/063* (2013.01); *B01J 35/004* (2013.01); *B01J 35/006* (2013.01); *B01J 35/0013* (2013.01); *B01J 35/1061* (2013.01); *B01J 37/0072* (2013.01); *B01J 37/0215* (2013.01); *B01J 37/344* (2013.01); *C01B 3/042* (2013.01); *C01B 3/10* (2013.01); *C01B 13/0207* (2013.01); *C07B 33/00* (2013.01); *C07D 301/03* (2013.01); *B01J 35/002* (2013.01); *Y02E 60/36* (2013.01)

(58) Field of Classification Search
None
See application file for complete search history.

(56) References Cited

U.S. PATENT DOCUMENTS

| | | |
|---|---|---|
| 6,492,014 B1 | 12/2002 | Rolison et al. |
| 7,081,433 B2 | 7/2006 | Rolison et al. |

(Continued)

OTHER PUBLICATIONS

Boccuzzi et al., J. Phys. Chem. 1996, 100, 3617-3624.

(Continued)

*Primary Examiner* — Kishor Mayekar
(74) *Attorney, Agent, or Firm* — US Naval Research Laboratory; Joseph T. Grunkemeyer

(57) ABSTRACT

A composition having: titania aerogel having titania nanoparticles and copper nanoparticles. Each of the copper nanoparticles is in contact with more than one of the titania nanoparticles. A method of: providing a titania aerogel, and forming or depositing copper nanoparticles onto the surface of the titania aerogel.

15 Claims, 14 Drawing Sheets

(51) Int. Cl.
- *C01B 13/02* (2006.01)
- *C07B 33/00* (2006.01)
- *B01J 21/06* (2006.01)
- *B01J 37/00* (2006.01)
- *B01J 35/10* (2006.01)
- *C01B 3/04* (2006.01)

(56) References Cited

U.S. PATENT DOCUMENTS

| | | | |
|---|---|---|---|
| 7,541,012 B2 | 6/2009 | Yeung et al. | |
| 8,143,185 B2 | 3/2012 | Rajeshwar et al. | |
| 8,155,485 B2 | 4/2012 | Hyde | |
| 2003/0187294 A1 | 10/2003 | Hagemeyer et al. | |
| 2013/0081692 A1 | 4/2013 | Ihara et al. | |
| 2014/0065290 A1* | 3/2014 | Lewis | B82Y 30/00 427/1 |
| 2015/0072164 A1 | 3/2015 | Petralia | |
| 2016/0030908 A1* | 2/2016 | Horvath | B82Y 30/00 429/231.5 |

OTHER PUBLICATIONS

Boccuzzi et al., J. Catal. 165, 129-139 (1997).
Then et al., Langmuir 2012, 28, 9996?10006.
Desario et al., J. Phys. Chem. C 2015, 119, 17529?17538.
Desario et al., Nanoscale, 2013, 5, 8073.
Gonzalez-Posada et al., RSC Adv., 2014, 4, 20659.
Kazuma et al., Nanoscale, 2011, 3, 3641.
Kum et al., Nanotechnology 26 (2015) 125402.
Morris et al., Science, 284, 622-625 (1999).
Panayatov et al., J. Phys. Chem. C 2013, 117, 15035?15049.
Pietron et al., Nano. Lett. 2, 545-549 (2002).
Pietron et al. J. Non-Cryst. Solids 285 (2001) 13-21.
Nu et al., Catal. Sci. Technol., 2011, 1, 601-608.
Yamaguchi et al., Chem. Lett. 2012, 41, 13401342.
Zhang et al., Electrochem. Comm. 13 (2011) 861-864.
Zhang et al., Int. J. Hydrogen Energy 40 (2015) 303-310.
Search Report and Written Opinion in PCT/US2017/024719 (dated Jul. 7, 2017).
Rayalu et al., Appl. Catal. B: Environ. 142-143, 684-693 (Jun. 12, 2013).
Rolison et al., Science, 299, 1698-1701 (2003).
Choi et al., Int. J. Hydrogen Energy, 32, 3841-3848 (2007).
Search Report in EP17776538.5 (dated Aug. 27, 2019).
Orojlou et al., "Metal oxide/TiO2 nanocomposites as efficient adsorbents for relatively high temperature H2S removal" J. Natural Gas Sci. and Engin, 59, 363-373 (Sep. 22, 2018).
Kim et al., "Photocatalytic degradation of methanol on titania and titania-silica aerogels prepared by non-alkoxide sol-gel route" Topics in Catalysis, 44(4), 499-505 (Jul. 1, 2007).
Marimuthu et al., "Tuning Selectivity in Propylene Epoxidation by Plasmon Mediated Photo-Switching of Cu Oxidation State" Science, 339(6127), 1590-1593 (Mar. 9, 2013).
Search report in EP Appl. No. 17776538.5 (dated Aug. 27, 2019).
Orojlou et al., "Metal oxide/TiO2 nanocomposites as efficient adsorbents for relatively high temperature H2S removal" J. Nat. Gas Sci. Engin. 59, 363-373 (2018).
Marimuthu et al., "Tuning Selectivity in Propylene Epoxidation by Plasmon Mediated Photo-Switching of Cu Oxidation State" Science 339, 1590-1593 (2013).
Kim et al., "Photocatalytic degradation on methanol on titania and titania-silica aerogels prepared by non-alkoxide sol-gel route" Topics in Catalysis 44(4), 499-505 (2007).
Rayalu et al., "Photocatalytic water splitting on Au/TiO2 nanocomposites synthesized through various routes: Enhancement in photocatalytic activity due to SPR effect" Appl. Cat. B: Environ. 142-143, 684-693 (2013).

* cited by examiner

Cu/TiO$_2$

Profile

COPPER NANOPARTICLE-TITANIA COMPOSITE NANOARCHITECTURES

This application claims the benefit of U.S. Provisional Application No. 62/314,486, filed on Mar. 29, 2016. The provisional application and all other publications and patent documents referred to throughout this nonprovisional application are incorporated herein by reference.

TECHNICAL FIELD

The present disclosure is generally related to copper-titania composites.

DESCRIPTION OF RELATED ART

Copper nanoparticles supported on titanium oxide were first rigorously described in the mid-to-late 1990s, with emphasis both on their structural characterization and on their application as carbon monoxide (CO) oxidation catalysts (Bocuzzi et al., *J. Phys. Chem.* 100 (1996) 3617-3624; Bocuzzi et al., *J. Catal.* 165 (1997) 129-139). Both metallic and oxidic Cu species were evident in the $TiO_2$-supported Cu nanoparticles (Bocuzzi, *J. Catal.*). More recent attempts to decisively determine the active site(s) for CO oxidation at $Cu/TiO_2$ composites have produced ambiguous results: $Cu^{+1}$ is implicated in several studies (Chen et al., *Langmuir* 28 (2012) 9956-10006; Wu et al., *Catal. Sci. Technol.* 1 (2011) 601-608; Chen et al., *Catal. Commun.* 9 (2008) 2381-2385), but metallic Cu also likely plays a critical role (Wu).

Surface plasmon resonance-driven photocatalysis can occur at $Cu/TiO_2$ materials under visible-light irradiation (Zhang et al., *Int. J. Hyd. Energy* 40 (2015) 303-310; Yamaguchi et al., *Chem. Lett.* 41 (2012) 1340-1342). While SPR-driven photocatalysis has been extensively investigated using Au or Ag nanoparticles as the SPR-active sensitizer of the supporting semiconductor, especially $TiO_2$ (Linic et al., *Nature Mater.* 14 (2015) 567-576; Dodekatos et al., *Top. Curr. Chem.* 371 (2016) 215-252; Lou et al., *ChemCatChem* 6 (2014) 2456-2476; Hou et al., *Adv. Funct. Mater.* 23 (2013) 1612-1619; Warren et al., *Energy Environ. Sci.* 5 (2012) 5133-5146; Zhou et al., *J. Mater. Chem.* 22 (2012) 21337-21354; Linic et al., *Nature Mater.* 10 (2011) 911-921; Primo et al., *Phys. Chem. Chem. Phys.* 13 (2011) 886-910), reports in which the more economical Cu serves as the plasmonic sensitizer are far fewer (Zhang, Yamaguchi). Copper nanoparticles oxidize easily (Kaatz et al., *Appl. Phys. Lett.* 61 (1996) 3807-3809); the only report unambiguously demonstrating SPR-driven photocatalysis at supported Cu nanoparticles also describes the necessity of protecting the Cu nanoparticles with a polymeric layer to prevent oxidation of the nanoscale metallic Cu (Yamaguchi).

BRIEF SUMMARY

Disclosed herein is a composition comprising: titania aerogel comprising titania nanoparticles and copper nanoparticles. Each of the copper nanoparticles is in contact with more than one of the titania nanoparticles.

Also disclosed herein is a method comprising: providing a titania aerogel, and forming or depositing copper nanoparticles onto the surface of the titania aerogel.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

Figure 1A:
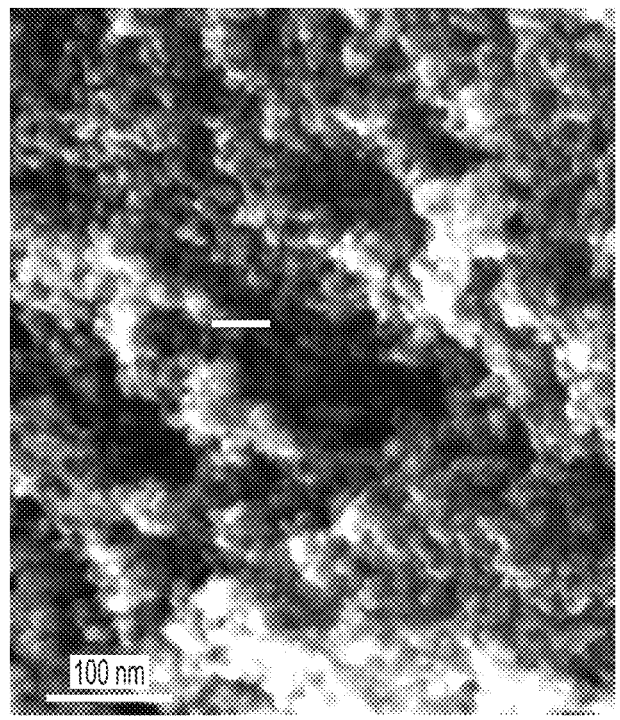
FIGS. 1A-B show a scanning electron micrograph of titania aerogel (FIG. 1A) and a schematic representation (FIG. 1B) of $Cu$—$TiO_2$ aerogel showing the extensive contact between the $TiO_2$ nanoscale network and the supported Cu nanoparticles.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

A composite ultraporous material designated as $Cu$—$TiO_2$ aerogel synthesized by photodepositing ~2-nm diameter copper (Cu) nanoparticles at pre-formed $TiO_2$ aerogels can be highly active for surface plasmon resonance (SPR)-driven photocatalytic oxidation of methanol ($CH_3OH$) under visible illumination in aqueous electrolyte. Further, the $Cu$—$TiO_2$ composite aerogel is highly stable against corrosion of Cu(0) in the Cu nanoparticle to oxidized forms of Cu. The stabilization of Cu nanoparticles in primarily metallic form at oxide-based supports without ligand stabilizers is to date unique to the $Cu$—$TiO_2$ aerogel architecture. An extended $CuITiO_2$ interface arises as a result of depositing copper at the surface of the $TiO_2$ nanoparticulate-bonded solid network within the mesoporous architecture. More explicitly, the $TiO_2$ aerogel comprises nanostructured pore-solid bicontinuous networks in which the particles comprising the titania network can contact the Cu nanoparticle surface at multiple points, creating multiple reactive interfaces, without occluding the entire Cu nanoparticle surface from the gas or liquid reaction medium that fills the pores of the catalytic aerogel during catalytic operation. A stable, visible light-active photocatalytic architecture that utilizes non-precious metals such as Cu as plasmonic sensitizers should enable: (1) sunlight-driven photocatalytic degradation of environmental pollutants and chemical threat agents; (2) photocatalytic generation of hydrogen ($H_2$) fuel using only renewable feedstocks such as water and sunlight; (3) creation of small-molecule oxidation catalysts for both degradation of environmental pollutants and oxidation of feedstocks like ethylene and propylene to high-value epoxides under straightforward non-photochemical (thermal) heterogeneous catalysis conditions at low temperatures; and (4) sunlight-driven photocatalytic generation of carbon-based fuels using only renewable feedstocks such as water and carbon dioxide ($CO_2$). Catalytic applications (1-3) are well-developed and well-understood when using gold (Au) and silver (Ag) as the oxide-supported plasmonic and/or catalytic nanoscale metal. The presently disclosed composition is a stable plasmonic catalytic nanoarchitecture requiring no precious metals and no additional chemical stabilizers.

The ideal Cu-based plasmonic photocatalyst would function durably without the necessity of adding chemical stabilizers and would be storable indefinitely under ambient conditions. One strategy to stabilize Cu nanoparticles would be to cathodically protect metallic Cu by establishing extensive contact with a reducing support. Metallic Cu is stabilized to some extent against oxidation at the $CuITiO_2$ interface (Fu et al., *Surf. Sci. Rep.* 62 (2007) 431-498). An arrangement on the nanoscale of $Cu+TiO_2$ in which multiple $CuITiO_2$ contacts exist per Cu nanoparticle could significantly stabilize Cu nanoparticles against oxidation and keep them in primarily metallic form. Such stabilization would enable exploitation of the SPR response of Cu to drive photochemistry under practical conditions, as well as create a $Cu/TiO_2$ catalytic architecture with higher metallic Cu content than previously possible, thereby yielding improved catalytic performance (in terms of reactivity and selectivity) than achievable with $Cu/TiO_2$ forms described to date.

Figure 1B:
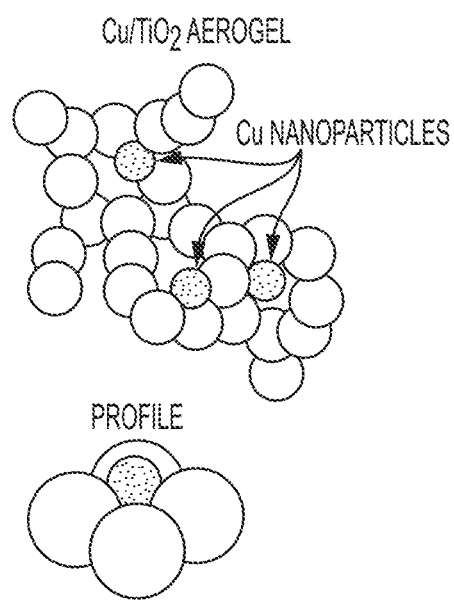
Figure 2A:
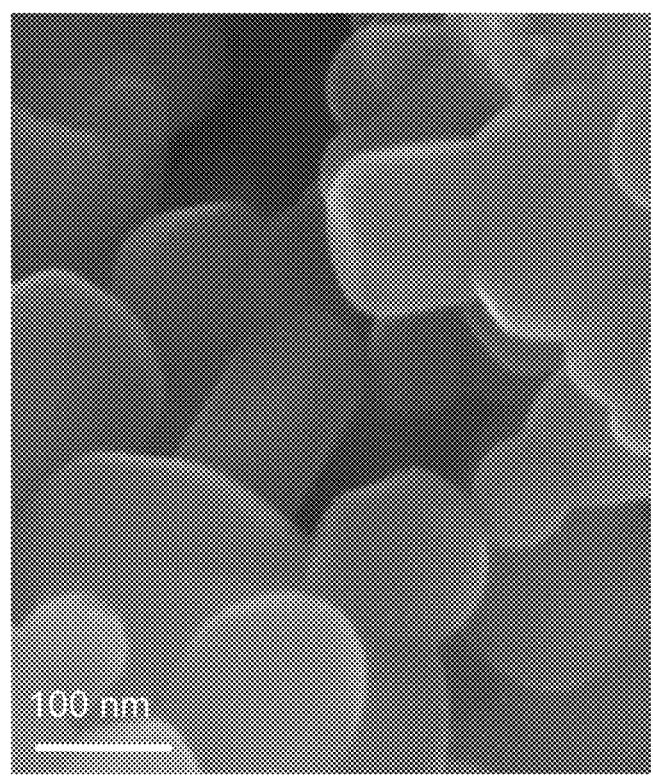
FIGS. 2A-B show show a scanning electron micrograph of commercial nanoparticulate titania (FIG. 2A) and a schematic representation (FIG. 2B) of a conventional $Cu/TiO_2$ nanocomposite, illustrating the single interfacial boundary between the Cu nanoparticles and the $TiO_2$ support.
Figure 2B:
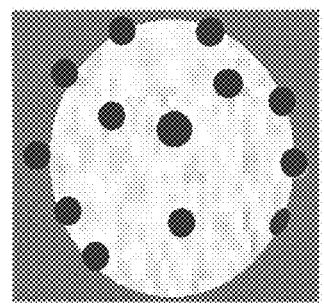
Figure 2B:
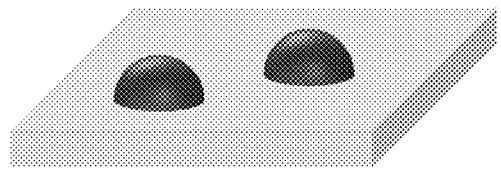

As established below, photodeposition of Cu at $TiO_2$ aerogels surfaces produces catalytic $Cu$—$TiO_2$ nanoarchitectures in which nanometer-scale Cu nanoparticles contact the 10-15-nm, covalently bonded $TiO_2$ nanoparticles at multiple points (FIGS. 1A-B). Such an arrangement, reported previously when describing catalytic $Au$—$TiO_2$ aerogels (DeSario et al., *Nanoscale* 5 (2013) 8073-8083; Panayotov et al., *J. Phys. Chem. C* 117 (2013) 15035-15049; Pietron et al., *Nano. Lett.* 2 (2002) 545-549; U.S. Pat. No. 7,081,433, 25), strongly contrasts structurally with the more conventional approach of depositing metals on non-networked nanoscale oxides (FIGS. 2A-B). The most critical difference in the two arrangements of nanoscale Cu with nanoscale $TiO_2$ is that the more conventional approach produces only one interface—a one-dimensional line boundary—between the catalytic metal nanoparticle and the oxide support. While the structure of the catalytic nanoparticle/support interface has significant implications for catalytic activity for supported metal nanoparticle catalysts in general, in the case of supported Cu nanoparticles, it is important to stabilize Cu in metallic form.

Figure 15:
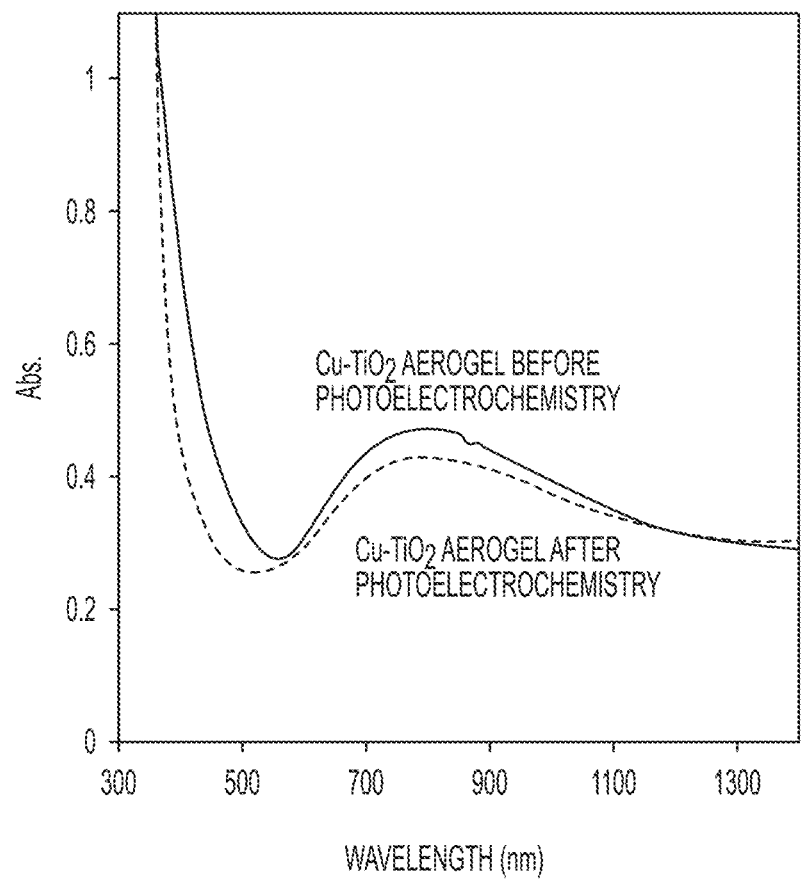
FIG. 15 shows diffuse reflectance UV-visible spectroscopy of Cu nanoparticle-modified $TiO_2$ aerogels fabricated by photocatalytic reduction of $Cu(NO_3)_2$ at the $TiO_2$ surface before (top) and after (bottom) photoelectrochemical application.

The following has been demonstrated: (i) photodeposition of small (primarily ~2 nm) Cu nanoparticles at $TiO_2$ aerogels to create catalytic $Cu$—$TiO_2$ aerogels; (ii) a strong SPR feature corresponding to Cu nanoparticles in extensive contact with the supporting $TiO_2$ aerogel; (iii) SPR-driven photocatalytic oxidation of methanol at the catalytic $Cu$—$TiO_2$ aerogels; and (iv) stability of the Cu nanoparticles against oxidation both during storage in ambient air and under catalytic operatic conditions, as seen by the similarity of the SPR signature of the $Cu$—$TiO_2$ aerogels before and after operation (FIG. 15). The results highlight the opportunities inherent to this 3D catalytic architecture as: (i) a durable, visible light-active photocatalyst; (ii) an economical catalyst for low-temperature oxidative degradation of pollutants, toxic industrial chemicals, and chemical threat agents; and (iii) a low-temperature selective epoxidation catalyst for olefins.

In general, aerogels are nanoscopic pore-solid architectures with high surface area (e.g., 150-1000 $m^2/g$) and a continuous mesoporous network. Titania aerogels may be made by methods disclosed in Pietron et al., *J. Non-Cryst. Solids*, 285 (2001) 13-21. In one example method, absolute ethanol and titanium(IV) isopropoxide are added to a stirred mixture of $H_2O$, absolute ethanol, and 70% nitric acid. A firm, clear gel is formed, covered and aged overnight, and quenched with acetone. The gel is washed in an acetone:water mixture to remove byproducts and residual reagents. The wet gel is then loaded under acetone into a supercritical dryer and rinsed with liquid $CO_2$ (several rinsings over ~4 h) before taking the liquid $CO_2$ above its critical temperature and pressure ($T_c=31°$ C., $P_c=7.4$ MPa). The aerogel may be dried, heat-treated, and ground to a powder.

The titania aerogels comprise nanoparticles of titania. Copper nanoparticles may then be formed in the aerogel or deposited on the aerogel. This protocol allows each of the copper nanoparticles to be in contact with more than one of the titania nanoparticles. There may be other copper nanoparticles present in the composition that do not contact more than one titania nanoparticle, as long as least some of the copper nanoparticles have this property.

The copper nanoparticles may comprise less than 15, 11, or 10 wt % of copper oxide on average. The average may include any copper nanoparticles that do not contact more than one titania nanoparticle. The copper nanoparticles may be free of, or comprise on average less than 10 wt % of stabilizing ligands or other organic compounds on the surfaces of the nanoparticles. Stabilizing ligands are molecules on the surface of the nanoparticle that tend to prevent oxidation of the copper, such as polyvinyl alcohol. One example method for forming the copper nanoparticles is photodeposition as described below.

A variety of reactions, including catalyzed reactions and surface plasmon resonance-driven reactions may be performed using the composition. Example reactions include, are not limited to, oxidation of water, ethylene, propene, and alcohols such as methanol.

Figure 3:
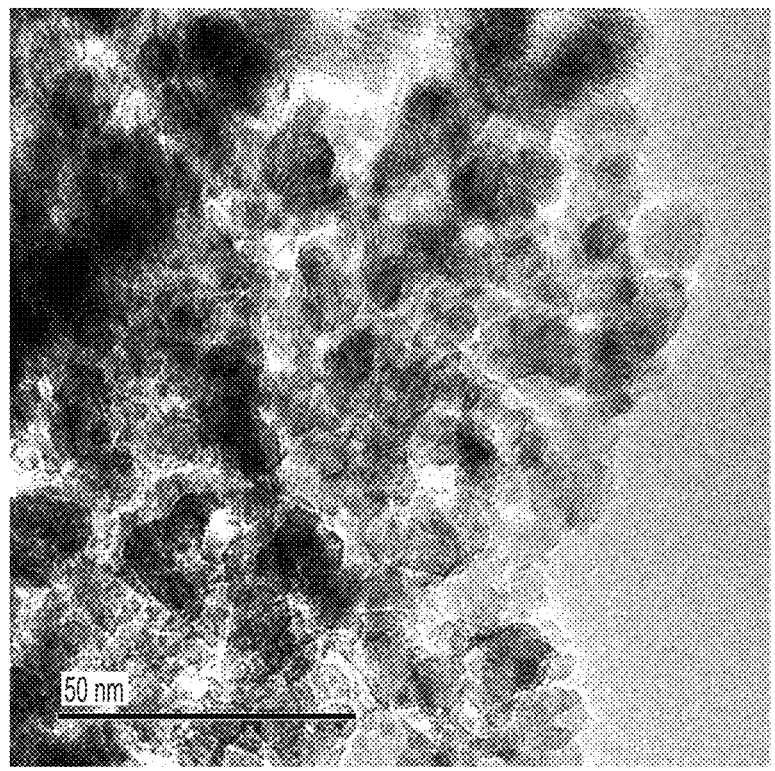
FIG. 3 shows a transmission electron micrograph of $Cu$—$TiO_2$ aerogel.
Figure 4:
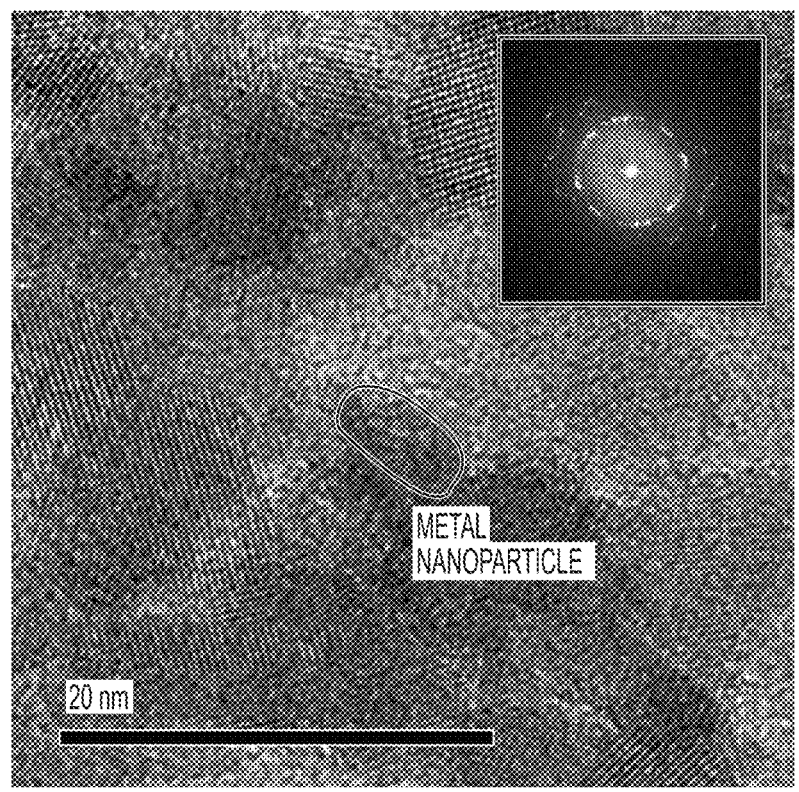
FIG. 4 shows a high-resolution transmission electron micrograph (HRTEM) of a metal nanoparticle in an anatase titania aerogel. Metallic nanoparticle (outlined) was identified using a fast-fourier transform (FFT) technique in which FFT (shown in inset) is masked near known metallic lattice constants and then an inverse FFT is performed.

Deposition of Cu nanoparticles at $TiO_2$ aerogels—A procedure described by Wu et al. (*Catal. Sci. Technol.* 1 (2011) 601-608) was adapted to photodeposit Cu nanoparticles with ~2-nm diameters at the surface of $TiO_2$ aerogels with the intention of maximizing interfacial contact between the Cu particles and the nanostructured, 3D networked $TiO_2$ support. To execute the photodeposition, a 500-W Xe arc lamp was used to illuminate slurries of $TiO_2$ aerogel dispersed in an aqueous solution contain the Cu precursor as ionic Cu(II)/reactant slurries. Namely, ~150 mg of $TiO_2$ aerogel in 110 mL of 2 mM $Cu(NO_3)_2$ in 10:1 (vol:vol) $H_2O:CH_3OH$ (adjusted to pH 9.5±0.5) was illuminated for a period of either 6 h or 24 h. Transmission electron microanalysis of the $TiO_2$ aerogel after the photodeposition step reveals a nanostructured mesoporous composite (FIG. 3) with ~2-nm Cu particles deposited on the $TiO_2$ aerogel surface; metallic copper is evident from the characteristic lattice constants of Cu(111) in the Cu nanoparticles (FIG. 4).

Figure 5:
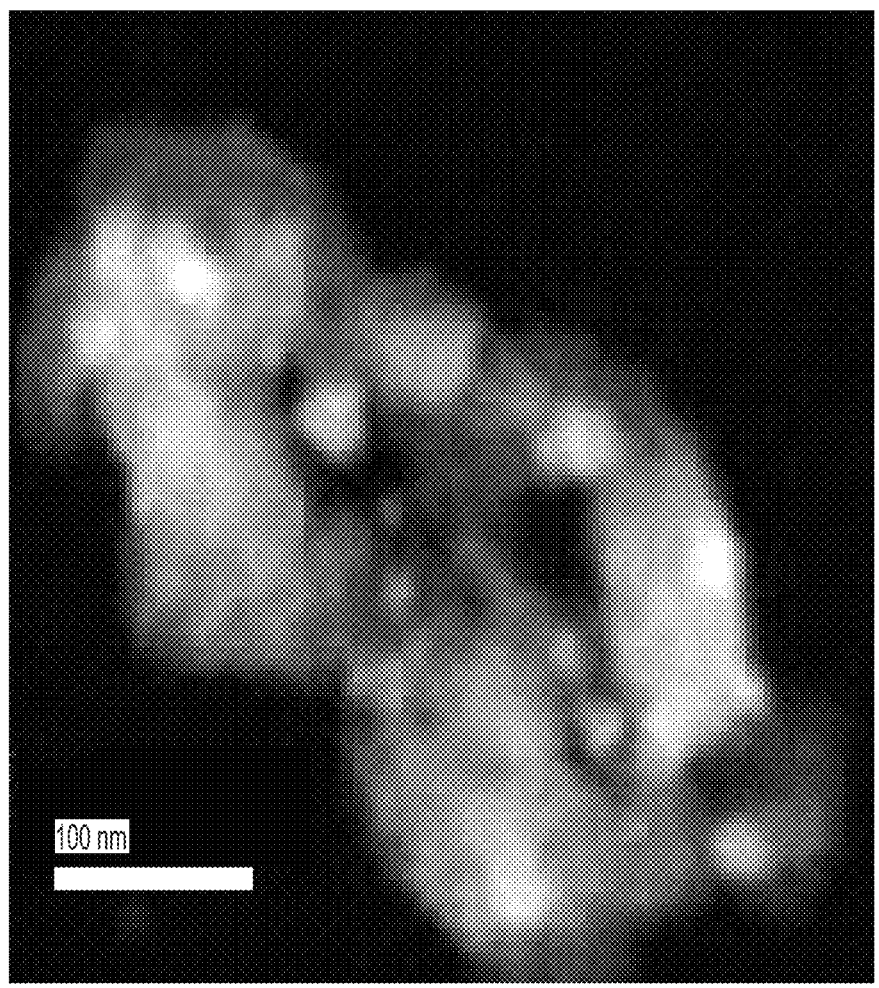
FIG. 5 shows a HAADF TEM of $Cu$—$TiO_2$ aerogel.
Figure 6:
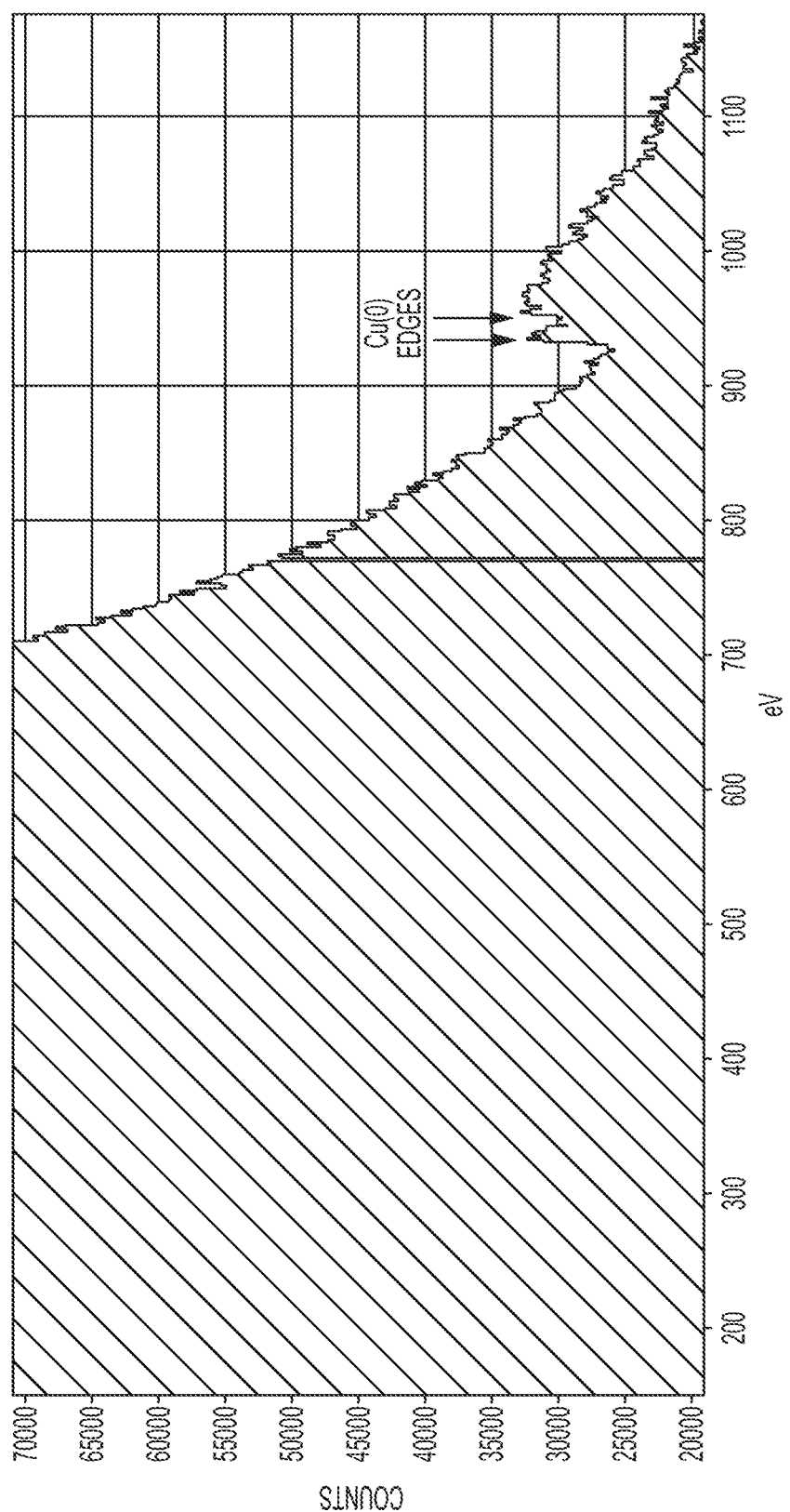
FIG. 6 shows electron energy-loss spectroscopy of $Cu$—$TiO_2$ aerogel.

Scanning transmission electron micrographs (FIG. 5) taken using a high-angle annular dark-field (HAADF) detector coupled with energy-dispersive spectroscopy (EDS) reveal the presence of copper distributed throughout the solid. Overlaying the EDS elemental maps for Ti, O, and Cu reveals little overlap between the Cu and O regions, indicating the presence of predominantly metallic copper nanoparticles in the Cu—$TiO_2$ aerogels. Electron energy-loss spectroscopy (EELS) of the Cu—$TiO_2$ aerogel (FIG. 6) produces a Cu L23 edge spectrum matching published reference spectra for metallic Cu, without the white line features associated with Cu oxides (Ahn et al., *EELS atlas: A reference collection of electron energy loss spectra covering all stable elements*, Warrendale: Gatan, 1983).

Figure 7:
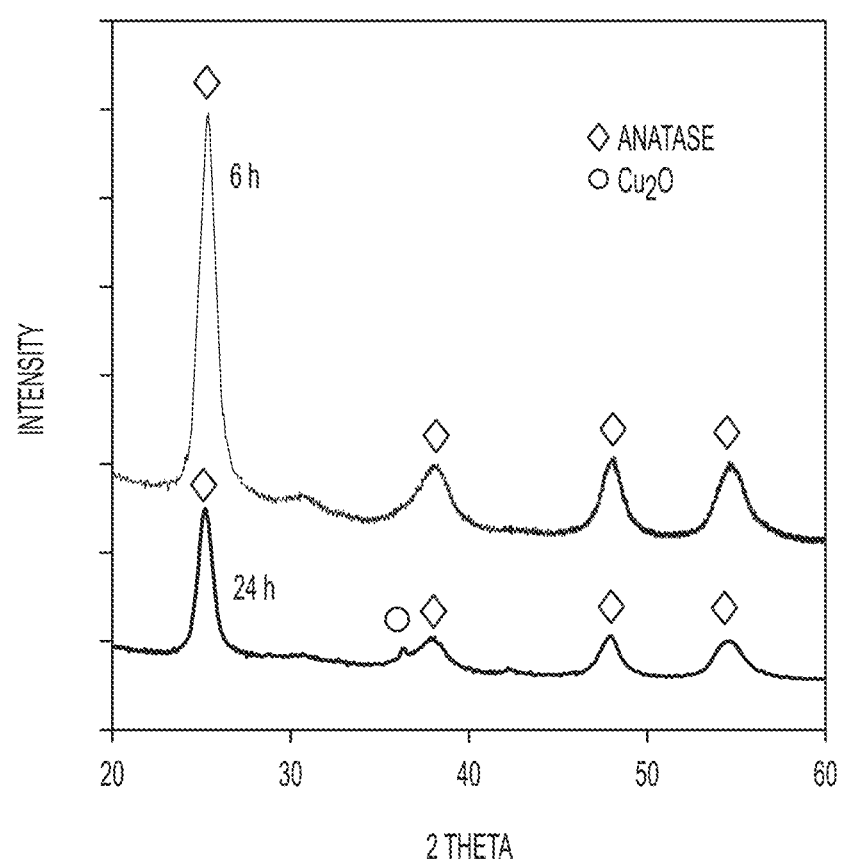
FIG. 7 shows X-ray diffractometry of $Cu$—$TiO_2$ aerogels fabricated by reductive photodeposition of Cu from $Cu(NO_3)_2$(aq) at UV-illuminated $TiO_2$ aerogel slurries under various conditions: (top) photoreduction for 6 h in Ar-saturated conditions; (bottom) photoreduction for 24 h in Ar-saturated conditions.

X-ray diffractometry—The $TiO_2$ nanoparticles comprising the nanostructured network in the Cu—$TiO_2$ aerogels are anatase in crystal habit (FIG. 7). Broad diffraction peaks characteristic of nanoparticulate anatase (JCPDS #01-075-2544) occur at 2θ=25.5°, 38.5°, 48°, and 54.5°. The Cu—$TiO_2$ aerogel fabricated using a 24-h photoreduction protocol (bottom curve), has just-detectable diffraction peaks at 2θ=35.3° and 42.4°, which are characteristic of $Cu_2O$ (JCPDS #01-073-6237). Reflections corresponding to metallic Cu are not evident, due to the small (~2 nm) size of the Cu nanoparticles, which broaden the diffraction peaks to an extent that make them undetectable by XRD.

Figure 8:
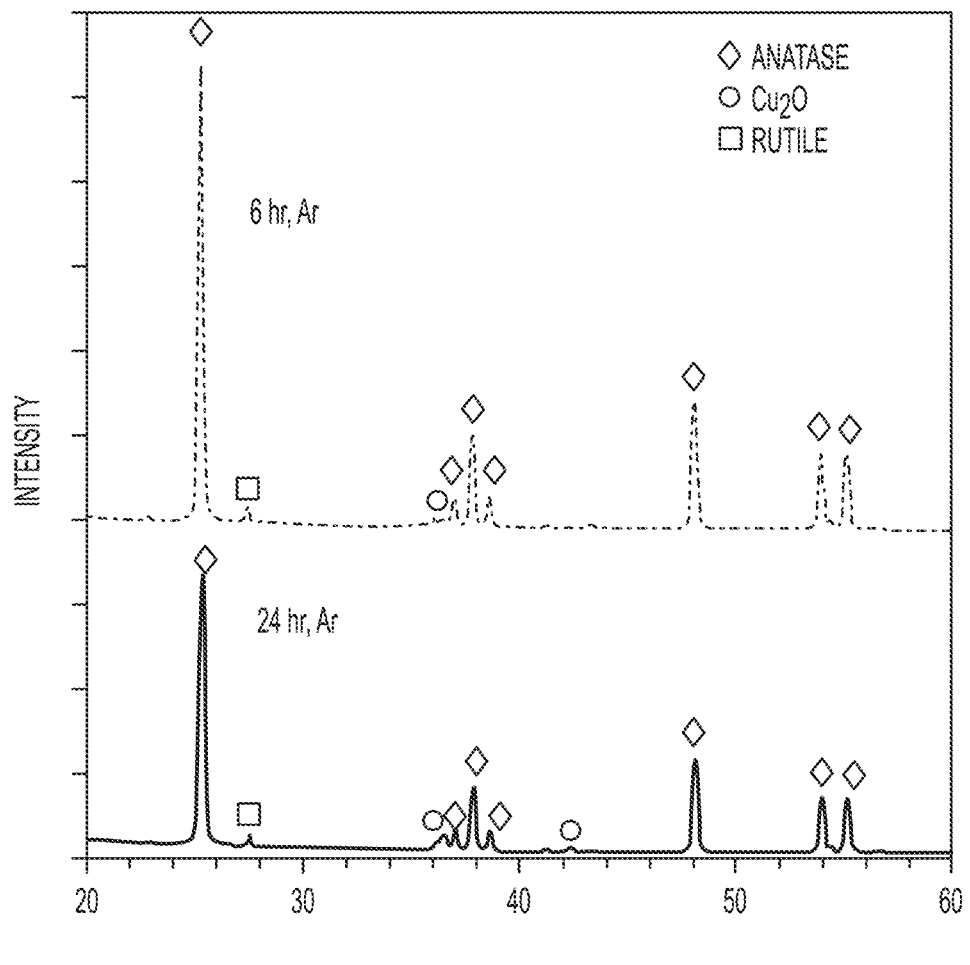
FIG. 8 shows X-ray diffractometry of $Cu/TiO_2$ composites fabricated by reductive photodeposition of Cu from $Cu(NO_3)_2$(aq) at UV-illuminated commercial anatase $TiO_2$ slurries: (top) photoreduction for 6 h in Ar-saturated conditions; (bottom) photoreduction for 24 h in Ar-saturated conditions.

X-ray diffractometry of Cu/$TiO_2$ composites derived from commercial anatase feature much sharper anatase peaks, once again at 2θ=25.5°, 38.5°, 48°, and 54.5° (FIG. 8). For both of the Cu/$TiO_2$ composites, weak but noticeable $Cu_2O$ diffraction peaks appear at 2θ=35.3° and 42.4°. The weak reflections for $Cu_2O$ in the Cu/$TiO_2$ composites are similar in appearance to those for the Cu—$TiO_2$ aerogels. However it is noteworthy that measurable $Cu_2O$ growth occurs in substantially shorter reaction times at commercial anatase than at $TiO_2$ aerogels when photochemically reducing $Cu(NO_3)_2$ at their respective surfaces. Although the evidence is qualitative, the XRD results for the two Cu/$TiO_2$ composite forms suggest that $TiO_2$ aerogel provides a local environment for reductive photodeposition of copper that inhibits oxide growth.

Figure 9:
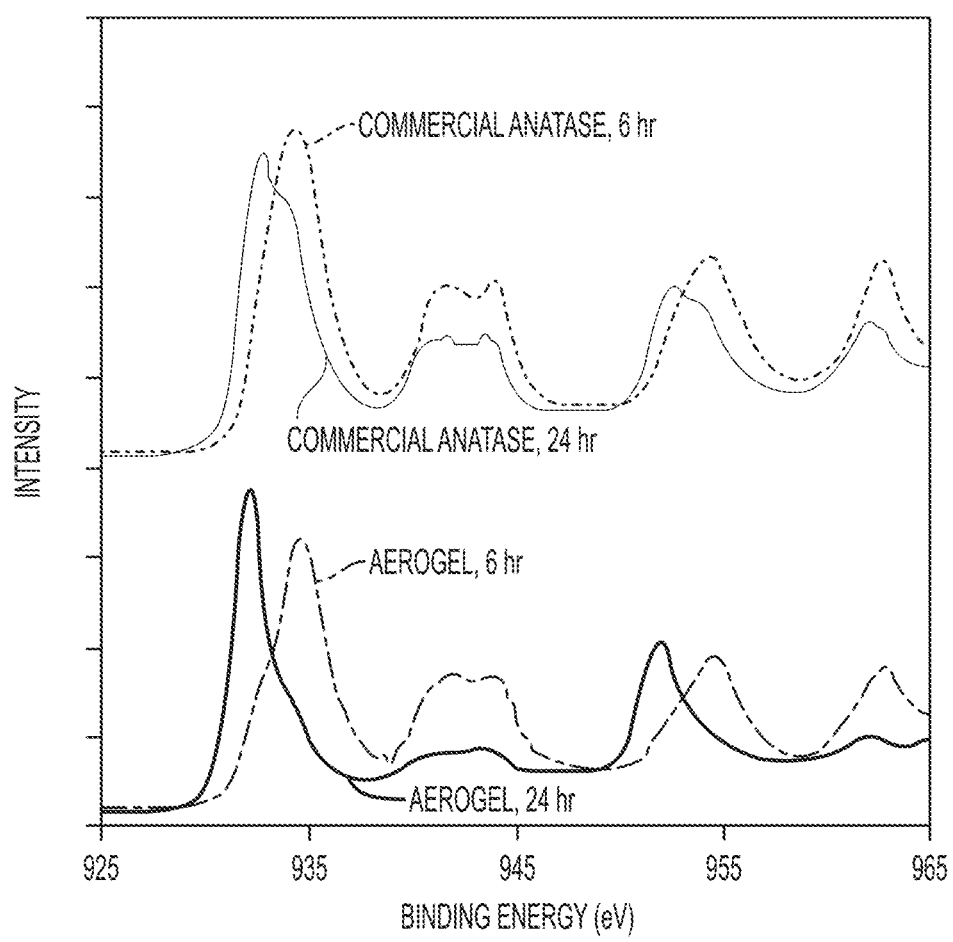
FIG. 9 shows X-ray photoelectron spectroscopy of $Cu/TiO_2$ composites comprising Cu photodeposited from 2 mM $Cu(NO_3)_2$ in Ar-saturated 10:1 (vol:vol) $H_2O:CH_3OH$ onto $TiO_2$ aerogel for 24 h; $TiO_2$ aerogel for 6 h; commercial anatase $TiO_2$ for 24 h; commercial anatase $TiO_2$ for 6 h.

X-ray photoelectron spectroscopy—Both the oxide support (aerogel vs. commercial anatase) and the duration of photodeposition impact the oxidation state of Cu, as determined by X-ray photoelectron spectroscopy (FIG. 9).

Photoreduction of $Cu(NO_3)_2$ in Ar-saturated 10:1 (vol:vol) $H_2O:CH_3OH$ at $TiO_2$ aerogel yields a Cu—$TiO_2$ aerogel with strong peaks centered in the Cu2p window at binding energies (BE) of ~931 and ~951.5 eV. These values are characteristic of $Cu2p_{3/2}$ and $Cu2p_{1/2}$ transitions in Cu metal and $Cu_2O$, with weak features from 940-945 eV and 960-965 eV (FIG. 9, aerogel 24 h) that correspond to CuO shake-up satellite peaks (Tahir et al., *J. Phys.: Condens. Matter* 24 (2012) 174002). The ratio of the $Cu2p_{3/2}$ peak height to that of its respective satellite peak (similarly for $Cu2p_{1/2}$ and its satellite peak) indicates that the majority of the Cu is Cu(0) or Cu(I) rather than Cu(II).

If photoreduction of $Cu(NO_3)_2$ at $TiO_2$ aerogel is limited to 6 h, the primary $Cu2p_{3/2}$ and $Cu2p_{1/2}$ features occur at ~0.5 eV higher BE (FIG. 9, aerogel 6 hr) and the intensity ratio of the $Cu2p_{3/2}$ and $Cu2p_{1/2}$ peaks relative to their respective satellites is lower compared to that observed at the Cu—$TiO_2$ aerogels reduced for longer times—thus a higher fraction of oxidized CuO results when Cu—$TiO_2$ aerogels are fabricated with shorter photoreduction times. When $Cu(NO_3)_2$ is photoreduced at commercial anatase (FIG. 9, commercial anatase) the BEs of the $Cu2p_{3/2}$ and $Cu2p_{1/2}$ transitions is higher, and the relative intensity of these peaks to the corresponding satellite peaks is lower, compared to those observed at the aerogel materials. Thus, for a given photoreduction time, the commercial anatase-supported Cu yields more oxidized Cu nanoparticles with a higher fraction of CuO to Cu/$Cu_2O$.

The most straightforward interpretation of the XPS results suggests that in all cases cupric oxide (Cu(II) oxide) deposits initially from the $Cu^{2+}$ precursor aqueous solution, and that cuprous oxide (Cu(I) oxide) and metallic copper develop after longer photoreduction times. The photoreduction proceeds more extensively and rapidly at the $TiO_2$ aerogels. The three-dimensional mesoporous environment characteristic of $TiO_2$ aerogels (FIG. 1B) contains nanoscale environments that may promote growth of Cu nanoparticles with more extensive CuII$TiO_2$ contact than is possible at non-mesoporous $TiO_2$ nanomaterials.

Figure 10:
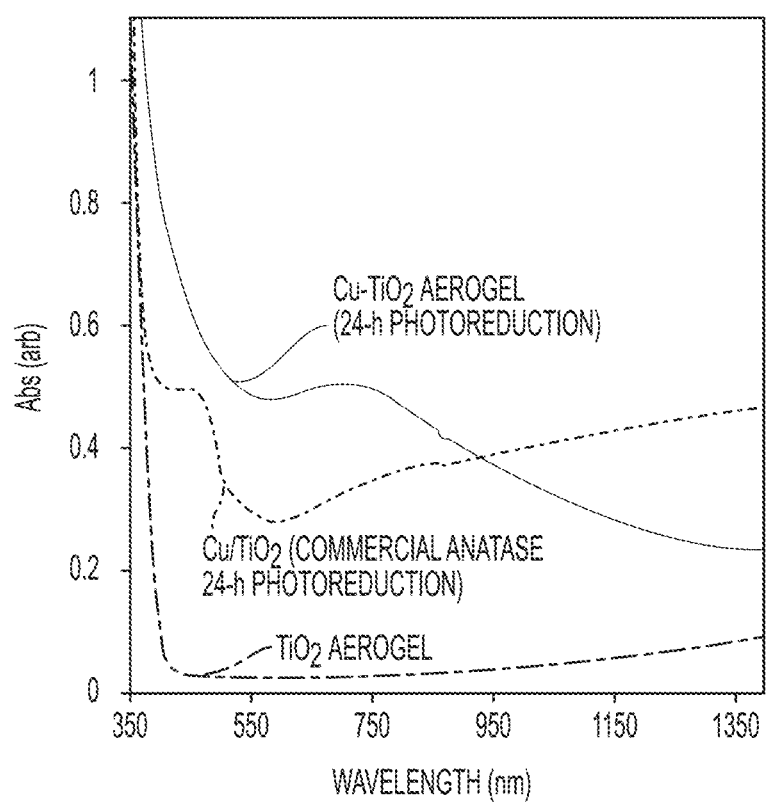
FIG. 10 shows diffuse reflectance UV-visible spectroscopy after 24 h of photocatalytic reduction of $Cu(NO_3)_2$ to yield $Cu$—$TiO_2$ aerogel (top); $Cu/TiO_2$ composite derived from commercial anatase $TiO_2$ powder (middle); and $TiO_2$ aerogel used as a Cu-free control (bottom).

Diffuse reflectance UV-visible spectroscopy of Cu—$TiO_2$ aerogels: Diffuse reflectance UV-visible spectroscopy of a Cu—$TiO_2$ aerogel reveals a strong surface plasmon resonance (SPR) feature centered at ~711 nm (FIG. 10, aerogel 24 hr). When $Cu^{2+}$ is photocatalytically reduced at non-mesoporous commercial anatase $TiO_2$, the dominant species that results is $Cu_2O$, as evidenced by the step-like feature in the spectrum at ~550 nm (FIG. 10, anatase 24 hr), consistent with the 2.2 eV band edge for $Cu_2O$ (Tahir et al., *J. Phys.: Condens. Matter* 24 (2012) 174002). For both of the Cu/$TiO_2$ composites, the absorbance arising from the composites is substantially greater than that for the bare $TiO_2$ aerogel control (FIG. 10, aerogel) at wavelengths longer than the anatase $TiO_2$ band edge at about ~385 nm Reported SPR maxima for Cu nano-objects (including nanoparticles, nanometer-scale disks and rods) fall between ~560-740 nm (Zhang et al., *Int. J. Hyd. Energy* 40 (2015) 303-310; Yamaguchi et al., *Chem. Lett.* 41 (2012) 1340-1342; Gonzalez-Posada et al., *RSC Advances* 4 (2014) 20659-20664; Susman et al., *Chem. Mater.* 24 (2012) 2501-2508; Kazuma et al., *Nanoscale* 3 (2011) 3641-3645; Rice et al., *J. Phys. Chem. C* 115 (2011) 1793-1799; Ghodselahi et al., *Physica B* 406 (2011) 2678-2683; Chan et al., *Nano Lett.* 7 (2007) 1947-1952). The multiple reports describing Cu nano-objects with SPR maxima at wavelengths >700 nm ascribe two critical factors that can drive the Cu SPR so far into the red: (1) the local dielectric constant surrounding the Cu nano-object; and (2) Cu particle shape. Although the size and shape of photodeposited Cu particles are broadly distributed in the Cu—$TiO_2$ aerogels, thereby broadening the SPR peak, the ~711 nm SPR maximum likely derives from an extended interfacial contact boundary between the Cu nanoparticles and the mesoporous $TiO_2$ aerogel support. The Cu nanoparticle nestled amidst the reticulated ~10-15 nm $TiO_2$ network is bathed in a mixed medium of air plus $TiO_2$, but a medium weighted more heavily toward the higher dielectric component ($TiO_2$) than is possible for Cu perched on ~10× larger commercial $TiO_2$ nanoparticles. Concomitantly, Cu in Cu—$TiO_2$ aerogels experiences a higher average dielectric constant relative to Cu/$TiO_2$ composites with only a single CuII$TiO_2$ interfaces.

Figure 11:
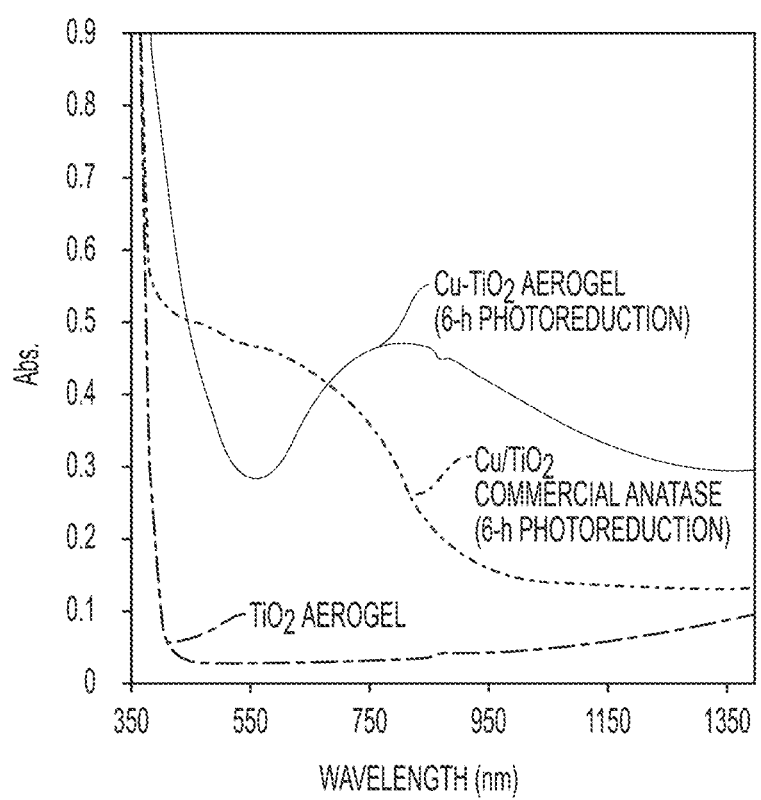
FIG. 11 shows diffuse reflectance UV-visible spectroscopy of Cu nanoparticle-modified $TiO_2$ materials fabricated by photocatalytic reduction of $Cu(NO_3)_2$ at the $TiO_2$ surface for short duration (6 h): $Cu$—$TiO_2$ aerogel (top); and $Cu/TiO_2$ composite derived from commercial anatase $TiO_2$ powder (middle); and $TiO_2$ aerogel used as a Cu-free control (bottom).
Figure 12:
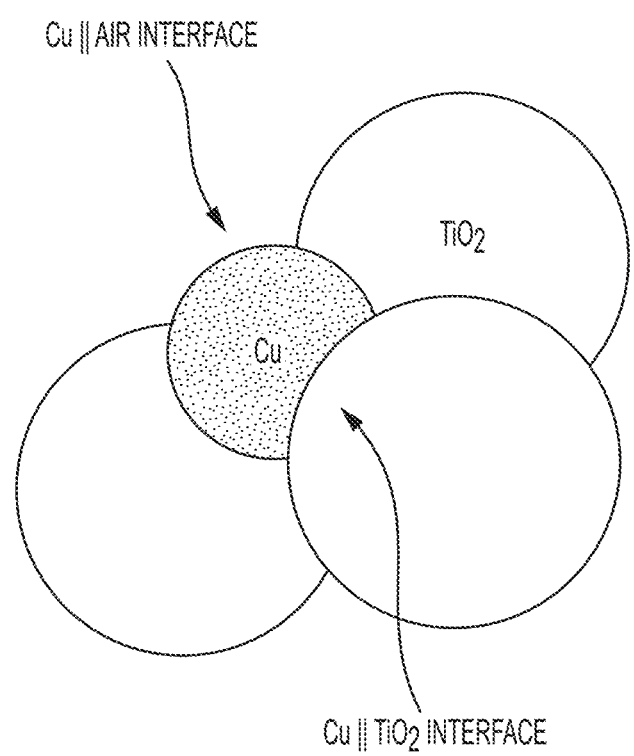
FIG. 12 shows a schematic representation of a segment of a $Cu$—$TiO_2$ aerogel illustrating the contact between a single Cu nanoparticle and multiple $TiO_2$ nanoparticles comprising part of the $TiO_2$ aerogel network and the portion of the Cu nanoparticle in contact with air.

Sensitivity of the Cu SPR to Cu oxidation state is evident in Cu—$TiO_2$ aerogels, consistent with prior reports of nanoscale Cu (Gonzalez-Posada et al., *RSC Advances* 4 (2014) 20659-20664; Ghodselahi et al., *Physica B* 406 (2011) 2678-2683; Chan et al., *Nano Lett.* 7 (2007) 1947-1952). When photocatalytic reduction of $Cu(NO_3)_2$ at the $TiO_2$ aerogel surface is performed for shorter duration (6 h), the Cu SPR peak appears at substantially lower energies, with the SPR maximum occurring at ~770 nm (FIG. 11). Mechanistically the 6- and 24-h results can be explained by $Cu^{2+}$ adsorbed at the $TiO_2$ surface initially converting to CuO (the $Cu^{+2}$ oxide), then photoreduced to $Cu_2O$ (the $Cu^{+1}$ oxide), and—in the aerogel—eventually converted to Cu metal given sufficient photoreduction time. The Cu nanoparticles in the aerogel likely exist in a mixed form, with the metallic phase forming first at the CuII$TiO_2$ interface with Cu oxides persisting at the Cullair interface on the nanoparticle (FIG. 12). Such an arrangement seems likely for two reasons: (1) conduction-band electrons generated during reductive photodeposition must flow from the $TiO_2$ conduction or surface trap states into the Cu adsorbate; and (2) the metallic state in Cu nanoparticles is stabilized at interfaces with reducing oxides such as $TiO_2$ (Fu et al., *Surf. Sci. Rep.* 62 (2007) 431-498). Given the substantial shift of the Cu SPR to 711 nm after 24 h of photoreduction (FIG. 10), it is likely that most of the $Cu_2O$ at the nanoparticlellair interface (FIG. 12) is converted to metallic Cu.

Figure 13:
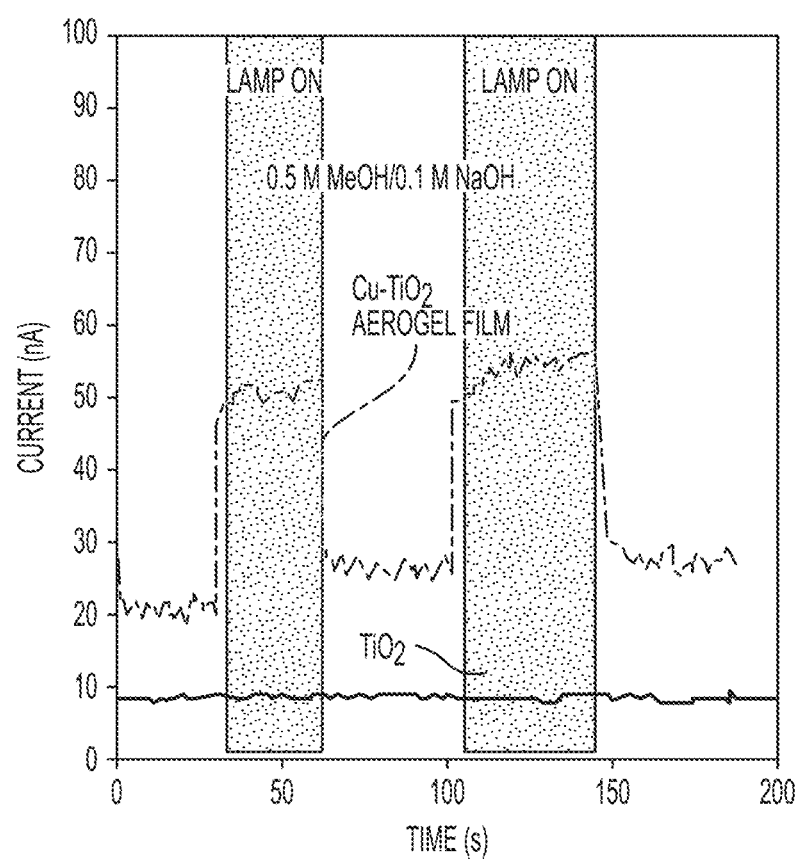
FIG. 13 shows photocurrents generated at $Cu$—$TiO_2$ aerogel (top) and $TiO_2$ aerogel (bottom) films on transparent FTO-coated glass electrodes in 0.5 M $CH_3OH$/0.1 M NaOH (aq) under alternating lamp on/lamp off conditions at $\lambda > 420$ nm.
Figure 14:
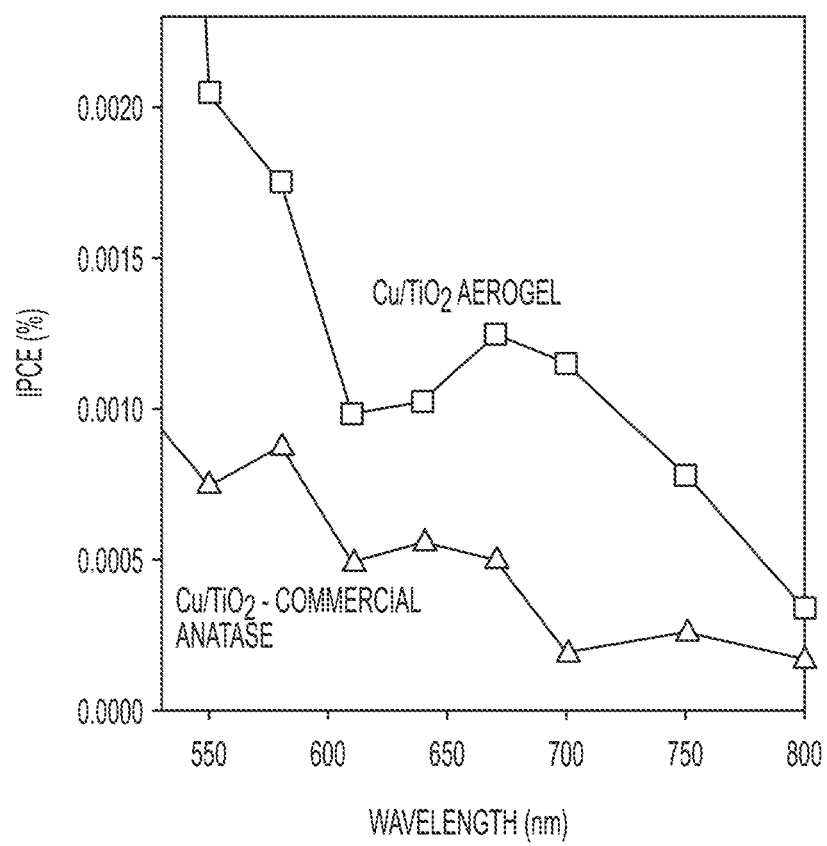
FIG. 14 shows photoaction spectra of photoelectrochemistry exhibited at photoanodes derived from $Cu$—$TiO_2$ aerogel films and $Cu/TiO_2$ (commercial anatase $TiO_2$) films in 0.5 M $CH_3OH$/0.1 M NaOH (aq).

Plasmonic photocatalysis at the CuII$TiO_2$ interface—Photoanodes comprising Cu—$TiO_2$ aerogel films deposited on transparent, conductive fluorine-doped tin oxide-coated glass electrodes oxidize methanol in basic aqueous electrolyte when illuminated with visible light, resulting in anodic photocurrents (FIG. 13, top). No photocurrents occur at photoanodes prepared using Cu-free $TiO_2$ aerogel under visible-light illumination (FIG. 13, bottom). Preliminary photoaction spectra reveal the onset of significant photocurrent at Cu—$TiO_2$ aerogel film photoanodes at wavelengths >650 nm. Photocurrent rises substantially at longer wavelengths, measured to date up to 700 nm (FIG. 14); in contrast, Cu/$TiO_2$ films with the semiconductor derived from commercial anatase $TiO_2$ exhibit a decaying photocurrent response between ~530-650 nm, with effectively no photocurrent response at longer wavelengths (FIG. 14). The incident photon-to-current efficiency (IPCE) as a function of wavelength for the two films correlates very strongly to the optical responses of the films as measured by diffuse reflectance UV-visible spectroscopy (FIG. 9). At the Cu—$TiO_2$ aerogel films, the photocurrent appears to be driven by the SPR response in the film because it correlates extremely well with the onset of the Cu SPR feature. The observed photoelectrochemical response is analogous to that observed for Au/$TiO_2$ photoelectrodes, for which it has been established that the SPR excitation is the driving force behind the observed photochemistry (Hou et al., *Adv. Funct. Mater.* 23 (2013) 1612-1619; Warren et al., *Energy Environ. Sci.* 5 (2012) 5133-5146) and to that observed for An—$TiO_2$ aerogel photoelectrodes for which it has been established that the SPR excitation is the driving force behind the observed photochemistry (DeSario et al., *Nanoscale* 5 (2013) 8073-8083). Copper oxides deposited at $TiO_2$ promote visible-light oxidation of organic compounds as well (Zhang et al., *Electrochem. Commun.* 13 (2011) 861-864; Xu et al., *Int. J. Hyd. Energy* 35 (2010) 5254-5261), often driven by direct excitation of the bandgaps of the various copper oxide species deposited at the $TiO_2$ surface (Xu).

Surface plasmon resonance—driven photochemistry at $TiO_2$-supported copper nanoparticles has been reported elsewhere (Zhang et al., *Int. J. Hyd. Energy* 40 (2015) 303-310; Yamaguchi et al., *Chem. Lett.* 41 (2012) 1340-1342). However, stability of the metallic phase of Cu in the Cu/$TiO_2$ has only been proven in cases where a polymer stabilizer was added to the Cu/$TiO_2$ composite (Yamaguchi). While visible-light photocatalysis has proven stable in some cases for extended reaction durations at Cu/$TiO_2$ composites with unprotected Cu, reports to date have described broadband visible light photocatalysis at unprotected Cu/$TiO_2$ (Zhang; Kum et al., *Nanotechnol.* 26 (2015) 125402); no action spectra were performed in these studies. Thus the durable, broadband visible-light photochemistry described therein as due to photocatalytic action could equally be due to activity of stable copper oxides, which have been shown elsewhere to be active for visible-light photocatalysis (Zhang et al., *Electrochem. Commun.* 13 (2011) 861-864).

The Cu—$TiO_2$ aerogel design embodies a new form of Cu-modified $TiO_2$ catalytic materials in which the pore-solid architecture of the aerogel stabilizes the metallic phase of the Cu nanoparticles better than any Cu/$TiO_2$ composite or other form of supported Cu nanoparticle composite reported to date. Even in the composite aerogel fabricated using short (6 h) photoreduction times, clear evidence of metallic Cu nanoparticles is evident by TEM, EDS, EELS, and electron-diffraction measurements (FIGS. 3-6) as well as in the SPR signature of the diffuse reflectance UV-visible spectra (FIG. 10) of Cu—$TiO_2$ aerogels. The metallic Cu phase of the Cu—$TiO_2$ aerogel is stable over the course of visible-light and UV spectroelectrochemical measurements, as measured via diffuse reflectance UV-visible spectroscopy of Cu—$TiO_2$ aerogel films taken both before and after the photoelectrochemical measurements (FIG. 15).

The stability of the metallic Cu particles is relevant to two classes of applications of catalytic Cu—$TiO_2$ aerogel architectures. The first application has been demonstrated here: exploitation of the Cu SPR feature to drive photocatalysis enabling harvesting of visible light (which comprises the most intense portion of the solar spectrum) and thereby driving photochemical reactions, potentially for the generation of fuels (photocatalytic water splitting to generate hydrogen) and for the degradation of harmful organic compounds, especially industrial pollutants and chemical warfare agents. To date, the majority of SPR-driven photocatalytic processes described in the literature employ precious metals such as Au and Ag as plasmonic sensitizers (Linic et al., Nature Mater. 14 (2015) 567-576; Dodekatos et al., Top. Curr. Chem. 371 (2016) 215-252; Lou et al., ChemCatChem 6 (2014) 2456-2476; Hou et al., Adv. Funct. Mater. 23 (2013) 1612-1619; Warren et al., Energy Environ. Sci. 5 (2012) 5133-5146; Zhou et al., J. Mater. Chem. 22 (2012) 21337-21354; Linic et al., Nature Mater. 10 (2011) 911-921; Primo et al., Phys. Chem. Chem. Phys. 13 (2011) 886-910), because the precious metals are substantially more stable to oxidation than non-precious metals such as Cu. Stabilization of Cu nanoparticles against oxidation enables exploitation of SPR for photocatalysis at considerably lower cost than composites featuring Au or Ag nanoparticles. The second application would be to use $Cu-TiO_2$ aerogels as heterogeneous catalysts for small-molecule oxidation. Metal oxide-supported Au nanoparticles have been extensively investigated in terms of their ability to perform small-molecule oxidation, especially oxidation of carbon monoxide (CO) (Widmann et al., Acc. Chem. Res. 47 (2014) 740-749; Christmann et al., ChemPhysChem 11 (2010) 1344-1363; Min et al., Chem. Rev. 107 (2007) 2709-2724; Janssens et al., Top. Catal. 44 (2007) 15-26; Chen et al., Acc. Chem. Res. 39 (2006) 739-746; Bond et al., Catal. Rev. Sci. Eng. 41 (1999) 319-388; Haruta et al., J. Catal. 144 (1993) 175-192) and the epoxidation of propylene (Kim; Bond; Nijhuis et al., Ind. Eng. Chem. Res. 45 (2006) 3447-3459; Hughes et al., Nature 437 (2005) 1132-1135; Hayashi et al., J. Catal. 178 (1998) 566-575). Numerous reports describe deposition of Cu on $TiO_2$ and other oxides and subsequent measurements of CO oxidation at the Cu/metal oxide composites (Bocuzzi et al., J. Phys. Chem. 100 (1996) 3617-3624; Chen et al., Langmuir 28 (2012) 9956-10006; Wu et al., Catal. Sci. Technol. 1 (2011) 601-608; Chen et al., Catal. Commun. 9 (2008) 2381-2385). Obtaining significant fractions of metallic Cu in the copper/copper oxide nanoparticles is a persistent challenge; adequate Cu content is critical to lowering the temperature of CO oxidation catalysis (a measure of the oxidative power of the composite catalyst) and concomitantly, rendering the composites reactive enough to execute the more challenging propene oxidation reaction (Marimuthu et al., Science 339 (2013) 1590-1593).

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:
1. A composition comprising:
   titania aerogel comprising titania nanoparticles;
      wherein the aerogel has a continuous mesoporous network; and
   catalytic nanoparticles comprising metallic copper;
      wherein the catalytic nanoparticles are distributed throughout the titania aerogel; and
      wherein each of the catalytic nanoparticles is in contact with more than one of the titania nanoparticles.
2. The composition of claim 1, wherein the catalytic nanoparticles comprise less than 15 wt % copper oxide.
3. The composition of claim 1, wherein the catalytic nanoparticles are free of stabilizing ligands.
4. The composition of claim 1, wherein the composition is made by a method comprising:
   providing the titania aerogel;
   forming or depositing the catalytic nanoparticles onto the titania aerogel.
5. The composition of claim 4, wherein the catalytic nanoparticles are formed by photodeposition.
6. The composition of claim 1, wherein the titania nanoparticles are 10-15 nm in size.
7. A method comprising:
   providing the composition of claim 1;
   performing a surface plasmon resonance-driven reaction on the composition.
8. The method of claim 7, wherein the reaction is oxidation of an alcohol.
9. The method of claim 7, wherein the reaction is oxidation of methanol.
10. The method of claim 7, wherein the reaction is oxidation of water.
11. The method of claim 7, wherein the reaction is oxidation of ethylene or propene.
12. A method comprising:
    providing the composition of claim 1;
    performing a catalyzed reaction on the composition.
13. The method of claim 12, wherein the reaction is oxidation of ethylene or propene.
14. A method comprising:
    providing a titania aerogel comprising titania nanoparticles;
       wherein the aerogel has a continuous mesoporous network; and
    forming or depositing catalytic nanoparticles comprising metallic copper onto the titania aerogel;
       wherein the catalytic nanoparticles are distributed throughout the titania aerogel; and
       wherein each of the catalytic nanoparticles is in contact with more than one of the titania nanoparticles.
15. The method of claim 14, wherein the catalytic nanoparticles are formed by photodeposition.

* * * * *